US009242248B2

(12) United States Patent
Astratov (10) Patent No.: US 9,242,248 B2
(45) Date of Patent: Jan. 26, 2016

(54) METHODS AND DEVICES FOR OPTICAL SORTING OF MICROSPHERES BASED ON THEIR RESONANT OPTICAL PROPERTIES (71) Applicant: Vasily N Astratov, Charlotte, NC (US)

(72) Inventor: Vasily N Astratov, Charlotte, NC (US)

(73) Assignee: The University of North Carolina at Charlotte, Charlotte, NC (US)

( * ) Notice: Subject to any disclaimer, the term of this patent is extended or adjusted under 35 U.S.C. 154(b) by 523 days.

(21) Appl. No.: 13/763,746

(22) Filed: Feb. 11, 2013

(65) Prior Publication Data

US 2014/0069850 A1 Mar. 13, 2014

Related U.S. Application Data (63) Continuation-in-part of application No. 13/614,156, filed on Sep. 13, 2012.

(51) Int. Cl.
*G01N 21/53* (2006.01)
*G02B 27/56* (2006.01)
(Continued)

(52) U.S. Cl.
CPC ............... *B03B 7/00* (2013.01); *B07C 5/3427* (2013.01); *G02B 27/56* (2013.01); *G01N 15/1436* (2013.01); *G01N 21/53* (2013.01); *G01N 2015/149* (2013.01)

(58) Field of Classification Search
CPC ........... G01N 2015/149; G01N 21/53; G01N 2015/1081; G01N 15/1436; G02B 6/29335; G02B 6/29341
USPC ................................................. 356/335–344
See application file for complete search history.

(56) References Cited

U.S. PATENT DOCUMENTS 3,710,933 A * 1/1973 Fulwyler ................ G01N 15/12
209/3.1
5,101,978 A * 4/1992 Marcus ................... B07C 5/342
209/3.1
(Continued)

FOREIGN PATENT DOCUMENTS

WO 2010141365 A2 12/2010

OTHER PUBLICATIONS

Li et al, "Evanescent light coupling and optical propelling of microspheres in water immersed fiber couplers", Laser Resonators Microresonators, and Beam Control VIX, 2012.*

(Continued)

*Primary Examiner* — Gregory J Toatley
*Assistant Examiner* — Jarreas C Underwood
(74) *Attorney, Agent, or Firm* — Clements Bernard PLLC; Christopher L. Bernard; Lawrence A. Baratta, Jr.

(57) ABSTRACT

Microspheres are sorted by resonant light pressure effects. An evanescent optical field is generated when light is confined within the interior of an optical element such as a surface waveguide, a tapered microfiber, or a prism. Microspheres brought within vicinity of the surface are subjected to forces that result from a coupling of the evanescent field to whispering gallery modes (WGM) in the microspheres. Alternatively, a focused laser beam is directed close to the edge of the microspheres to exert resonant optical forces on microspheres. Optical forces are resonantly enhanced when light frequencies match WGM frequencies in the microspheres. Those microspheres for which resonance is obtained are more affected by the evanescent field than microspheres for which resonance does not occur. Greater forces are applied to resonating microspheres, which are separated from a heterogeneous mixture according to size.

17 Claims, 9 Drawing Sheets

(51) Int. Cl.
  *B03B 7/00* (2006.01)
  *B07C 5/342* (2006.01)
  *G01N 15/14* (2006.01)

(56) References Cited

U.S. PATENT DOCUMENTS

| | | | | |
|---|---|---|---|---|
| 5,416,580 | A * | 5/1995 | Trainer | G01N 15/0211 356/336 |
| 5,752,606 | A * | 5/1998 | Wilson | H05H 3/04 209/2 |
| 6,815,664 | B2 * | 11/2004 | Wang | B07C 5/34 250/251 |
| 6,936,811 | B2 * | 8/2005 | Kibar | G01N 30/00 250/251 |
| 7,068,874 | B2 * | 6/2006 | Wang | H05H 3/04 250/432 R |
| 7,233,423 | B2 * | 6/2007 | Grier | H05H 3/04 359/15 |
| 7,241,988 | B2 * | 7/2007 | Gruber | G01N 15/1459 250/251 |
| 7,368,281 | B2 * | 5/2008 | Mozdy | G01N 33/54373 385/12 |
| 7,402,795 | B2 * | 7/2008 | Getin | B07C 5/00 250/251 |
| 7,511,263 | B2 * | 3/2009 | Getin | G01N 15/1434 204/157.15 |
| 7,574,076 | B2 * | 8/2009 | Mueth | G01N 21/0303 385/125 |
| 7,704,395 | B2 * | 4/2010 | Mueth | A61M 1/36 210/323.1 |
| 7,990,525 | B2 * | 8/2011 | Kanda | G01N 15/1429 356/73 |
| 8,231,833 | B2 * | 7/2012 | Maurer | G01N 21/552 204/450 |
| 8,515,227 | B2 * | 8/2013 | Sumetsky | G01N 21/05 250/227.24 |
| 8,552,363 | B2 * | 10/2013 | Erickson | B01L 3/502761 250/251 |
| 8,992,836 | B2 * | 3/2015 | Nitkowski | G01N 21/7746 385/12 |
| 9,012,830 | B2 * | 4/2015 | Zhu | G01N 21/7746 250/227.14 |
| 2003/0111594 | A1 * | 6/2003 | Getin | G21K 1/006 250/251 |
| 2005/0207940 | A1 * | 9/2005 | Butler | B01L 3/502761 422/73 |
| 2007/0086701 | A1 * | 4/2007 | Getin | G01N 15/14 385/37 |
| 2007/0237460 | A1 * | 10/2007 | Fan | G01N 21/7746 385/39 |
| 2012/0033915 | A1 * | 2/2012 | Erickson | G02B 6/122 385/42 |
| 2012/0196383 | A1 * | 8/2012 | Nitkowski | G01N 21/05 436/501 |

OTHER PUBLICATIONS

Kawata et al, "Movement of micrometer-sized particles in the evanescent field of a laser beam" Optics LEtters, vol. 17, No. 11, Jun. 1992.*

Ng et al. "Size-selective optical forces for microspheres using evanescent wave excitation of whispering gallery modes" Applied Physics Letters 92, 251109 (2008).

Xiao et al. "Whispering gallery mode enhanced optical force with resonant tunneling excitation in the Kretschmann geometry" Applied Physics Letters 94, 011102 (2009).

Ashkin et al., "Observation of Resonances in the Radiation Pressure on Dielectric Spheres" Physical Review Letters vol. 38, No. 23 (1977).

Brambilla et al. "Optical manipulation of microspheres along a subwavelength optical wire" Oct. 15, 2007 / vol. 32, No. 20 / Optics Letters.

MacDonald et al. "Microfluidic sorting in an optical lattice" Nature |vol. 426 | Nov. 27, 2003 www.nature.com/nature.

Fontes et al. "Double optical tweezers for ultrasensitive force spectroscopy in microsphere Mie scattering" Appl. Phys. Lett. 87, 221109 (2005).

Gaugiran et al. "Optical manipulation of microparticles and cells on silicon nitride waveguides" Sep. 5, 2005/ vol. 13, No. 18 / Optics Express 6956.

Schmidt et al. "Optofluidic trapping and transport on solid core waveguides within a microfluidic device" Oct. 29, 2007 / vol. 15, No. 22 / Optics Express 14322.

* cited by examiner

METHODS AND DEVICES FOR OPTICAL SORTING OF MICROSPHERES BASED ON THEIR RESONANT OPTICAL PROPERTIES

CROSS-REFERENCE TO RELATED APPLICATIONS

The present non-provisional patent application/patent is a continuation-in-part of co-pending U.S. patent application Ser. No. 13/614,156, filed on Sep. 13, 2012, and entitled "METHODS AND DEVICES FOR OPTICAL SORTING OF MICROSPHERES BASED ON THEIR RESONANT OPTICAL PROPERTIES," which claims the benefit of priority of U.S. Provisional Patent Application No. 61/535,409, filed on Sep. 16, 2011, and entitled "METHODS AND DEVICES FOR OPTICAL SORTING OF SIZE-MATCHED MICROSPHERES," the contents of both of which are incorporated in full by reference herein.

GOVERNMENT SUPPORT

This invention was made with Government support under award numbers ARO W911NF-09-1-0450 and NSF ECCS-0824067 by the Army Research Office and the National Science Foundation respectively. The Government has certain rights in the invention.

FIELD OF THE DISCLOSURE

The present disclosure relates generally to article sorting systems and methods. More particularly, the present disclosure relates to sorting microspheres by use of resonant optical forces.

BACKGROUND OF THE DISCLOSURE

Optical forces are applied in optical trapping, for example in optical tweezers. The effects of propelling microspheres in water due to evanescent fields are known. Weakly pronounced resonant peaks of optical forces have been observed in microdroplets. Some evidence for resonance force enhancement has been obtained in waveguide couplers and in the case of off-axially shifted focused beams. Using numerical modeling, high peak-to-background force ratios have been demonstrated in evanescent prism couplers. However, only a small enhancement in the optical force has been observed in the previous work. Although the possibility of using resonant optical forces was recognized, practical devices for sorting microspheres have not been previously proposed and developed.

BRIEF SUMMARY OF THE DISCLOSURE

In various exemplary embodiments, a method of separating and collecting microspheres is provided. The method includes propagating light within an interior of an optical element at a surface of the optical element, and providing a heterogeneous mixture of microspheres in the vicinity of the surface. An evanescent field exterior to the optical element is generated by the propagating light in a vicinity of the surface. Each microsphere has a size and a refractive index. Forces are applied on at least some of the microspheres by the evanescent field according to size and refractive index. The method further includes permitting movement of at least some of the microspheres upon which forces are applied by the evanescent field, thereby separating at least some of the microspheres of the heterogeneous mixture from a remainder of the mixture according to at least one of size and refractive index. Either the separated microspheres, the remainder of the mixture, or both, are collected.

In various other embodiments a system for separating and collecting microspheres includes an optical element having an interior bounded by a surface, and a light source, which is coupled to the optical element, propagating light within the interior at the surface, thereby generating an evanescent field exterior to the optical element in a vicinity of the surface. A heterogeneous mixture of microspheres flows exterior to the optical element in the evanescent field in the vicinity of the surface, each microsphere having a size and a refractive index. The evanescent field applies forces to at least some of the microspheres according to size and refractive index.

BRIEF DESCRIPTION OF THE DRAWINGS

The present disclosure is illustrated and described herein with reference to the various drawings, in which like reference numbers are used to denote like system components/method steps, as appropriate, and in which.

DETAILED DESCRIPTION OF THE DISCLOSURE

In various embodiments, new methods and systems are provided for optically sorting microspheres with similar or spectrally overlapping WGM positions based on resonant light pressure effects. These effects occur in an evanescent optical field generated when light is confined, such as by total internal reflection, within the interior of an optical element such as a surface waveguide, a tapered microfiber, or a prism. When light is confined or reflects internally at an outer surface of the optical element, the evanescent optical field extends from the surface into a limited vicinity external to the optical element. Microspheres brought within the vicinity of the surface, where the evanescent field is present, are subjected to forces that result from a coupling of the evanescent field to WGM modes in the microspheres. Optical forces are advantageously resonantly enhanced when frequencies of provided light and WGM frequencies in the microspheres are matched according to advancements described herein which were not previously known. Those microspheres for which resonance is obtained are more affected by the evanescent field than microspheres for which resonance does not occur. The principle of greater forces being applied to resonating microspheres is the basis for selectively separating matched microspheres from a heterogeneous mixture according to various embodiments described herein. A spectrally-narrow laser source is utilized in various embodiments to separate microspheres having WGM positions that overlap the emission line of the laser. In some embodiments, the evanescent optical field extends into an external medium which contains a heterogeneous mixture of microspheres. For example, microspheres are present in a microfluidic environment in some embodiments. In some examples, microspheres are present in air or vacuum exterior to the optical element in which light is confined, guided, reflected, or refracted. In some embodiments, resonant optical force can be exerted without using an intermediary optical element by focusing a laser beam close to the edge of microsphere where it can be efficiently coupled to WGMs.

Experimental observations include giant optical propelling velocities of approximately 0.45 mm/s for 15-20 µm polystyrene microspheres in microfiber couplers at modest guided powers of approximately 43 mW. Such velocities exceed previous observations by more than an order of magnitude and provide evidence for the existence of extraordinary strong resonant enhancement of optical forces. The magnitude of the peaks of resonant optical forces can approach theoretical limits imposed by the momentum conservation law on totally absorbing particles.

The magnitude of resonant optical force was a factor in developing a practical device for sorting microspheres based on whispering gallery mode (WGM) resonance. Very strong peak force magnitudes are required for achieving good selectivity. A key parameter determining the peak enhancement of resonant optical forces is represented by the quality factors (Q) of WGMs in microspheres. The magnitude of the resonant force increases with the Q-factor. One of the challenges in this area is connected with the fact that quality factors (Q) of WGMs in microspheres made from conventional materials such as silica or polystyrene are greatly diminished in a liquid environment due to reduced refractive index contrasts. For this reason, strong resonant enhancement of optical force has not been observed in previous studies performed mainly with small spheres with diameters below 10 µm. For such spheres, Q-factors are not sufficient for this effect to be pronounced. Furthermore, observation of this effect also involves measurements and treatment of experimental data aimed at determining maximal instantaneous velocities of microspheres as opposed to an average propelling velocity.

In at least some embodiments described herein, microspheres having similar or almost identical positions of WGM resonances are selected by use of a powerful light source with narrow spectral emission such as a laser. A tunable light source can be used to control the WGM resonant positions in selected spheres. An optical element provides confinement of light such as waveguide, a fiber, and a prism. A liquid or gas external medium or a vacuum can reside exterior to the optical element. A delivery system provides a flux of microspheres in the vicinity of the optical element within the evanescent optical field. Separation of size-matched microspheres occurs in a specially designed cell.

According to various methods and devices described herein, microspheres with positions of WGM spectral resonance that overlap the narrow emission line of a laser source are selected with high relative accuracy, approximately $1/Q$, where the Q can be larger than approximately $10^4$. Maximal resonant force can be realized if the laser emission line is spectrally narrower than the WGM resonance in microspheres. This condition is usually satisfied since the linewidth of the majority of laser sources is significantly narrower than 0.1 nm. Uniquely resonance-matched microspheres can be selected on a large scale. Embodiments described herein are applicable in liquid, gaseous (including air) and vacuum environments. In liquid, high index spheres (n>1.8) having high Q factors ($Q>10^4$) for small (approximately 10 µm) spherical cavities are used. Examples are given by barium-titanate glass and titania spheres with index of approximately 2. Examples also include polystyrene microspheres, having an index of approximately 1.6, with diameters in a range of approximately 3 to 20 µm. Smooth and well controlled flows of microspheres are advantageously provided in microfluidic environments. Optical tweezers may be used to control individual sphere trapping, releasing, and catching in the vicinity of an optical element such as a tapered fiber. High Q factors can be achieved by flowing microspheres in gaseous (including air) or vacuum environments.

Figure 1:
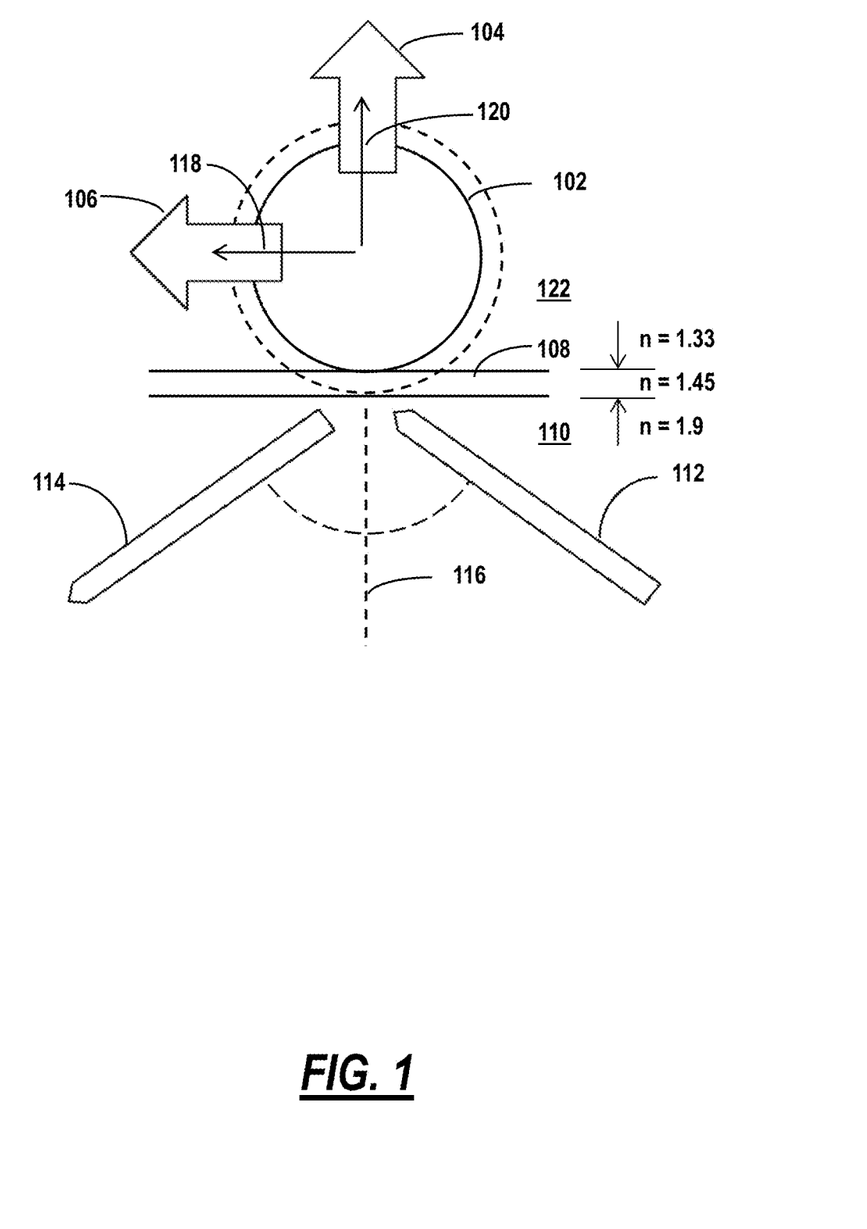
FIG. 1 is a diagram of a WGM coupling by which a microsphere is subjected to a vertical force and a horizontal force when a laser undergoes total internal reflection according to at least one embodiment.

FIG. 1 is a diagram of a WGM coupling by which a microsphere 102 is subjected to a vertical force 104 and a horizontal force 106 when a laser undergoes total internal reflection. A spacer 108, having an index of approximately 1.45, is provided over a substrate 110, having an index of approximately 1.9, in which an incoming ray 112 and a reflected ray 114 of the laser are directed at approximately 55 degrees from the internal normal 116. In order to create a strong resonant optical force, an efficient evanescent coupling between the confined waves in an optical element (tapered fiber, surface waveguide, or a prism) and WGMs in spheres is beneficial. FIG. 1 gives an example of a coupler using a prism with total internal reflection properties. For the evanescent wave excitation, there is a strong resonant horizontal scattering force 106, which acts on the sphere along the x-axis 118 when the frequency of the laser matches that for WGM. There is also a resonant vertical gradient force which acts on the sphere along the y-axis 120, due to the varying intensity of the evanescent field. Usually, dielectric objects with indexes higher than the environment tend to be attracted to high intensity regions of the electromagnetic field, which means attraction to the base of the prism. However, the opposite repulsive force is also possible. In FIG. 1, resonant light pressure effects are realized in a microfluidic environment 122, for example in which water having an index of approximately 1.33 is present.

Figure 2:
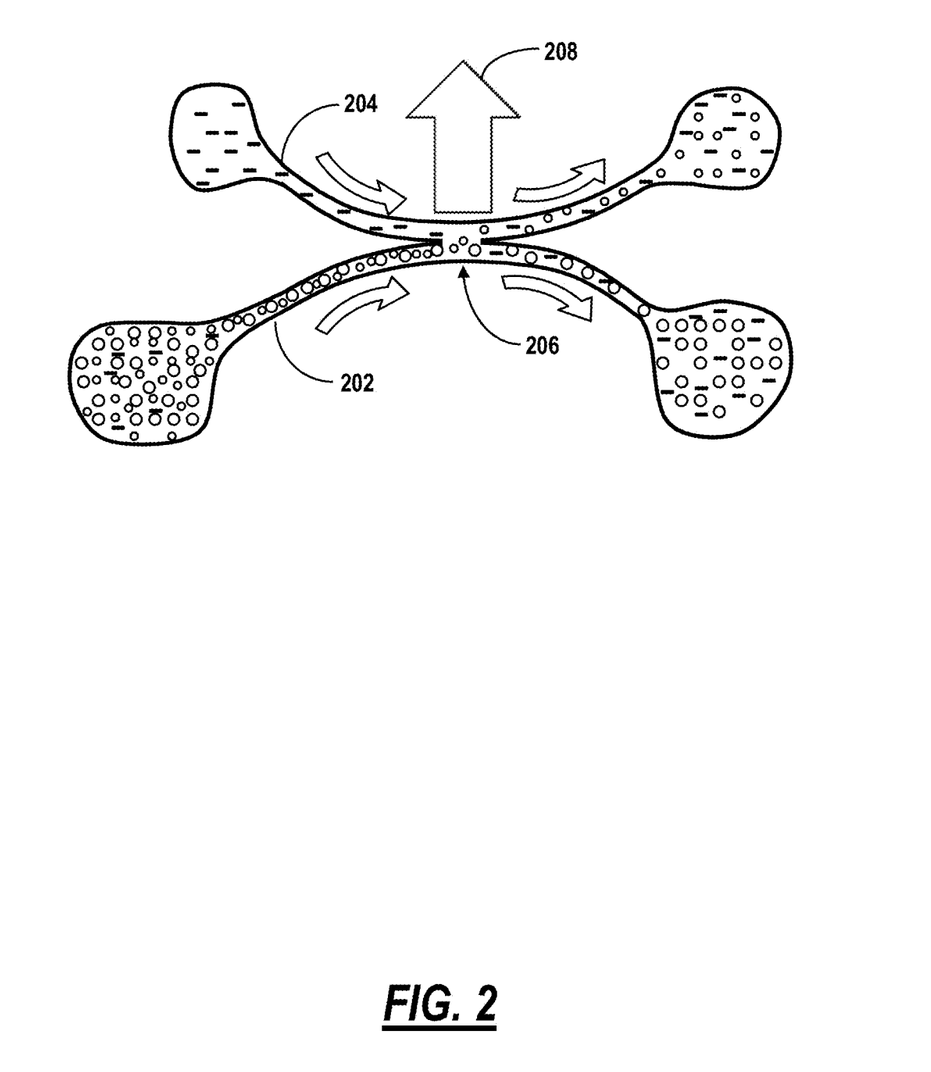
FIG. 2 is an illustration of the separating of microspheres by resonant optical forces in a microfluidic environment according to at least one embodiment.

FIG. 2 is an illustration of the separating of microspheres by resonant optical forces in a microfluidic environment according to at least one embodiment described herein. Microspheres are sorted according to the spectral positions of their WGM resonances in FIG. 2 at an overlap between two microfluidic flows, a flow within a lower branch 202 and a flow within an upper branch 204. Sorting occurs at a tangential point of contact 206 of the flows. As illustrated in FIG. 2, a heterogeneous mixture of microspheres is provided to the point of contact 206 by the lower branch 202. In microfluidics, the Reynolds numbers, which compare the effect of momentum of a fluid to the effect of viscosity, are typically very low. Consequently, side-by-side fluids do not necessarily mix in the traditional sense. Without additional optical forces, the spheres entrained within the incoming flow in the lower branch 202 would tend to stay in lower branch. However, under the influence of the resonant force 208, spheres of a certain size can move into the top branch 204, resulting in the sorting of microspheres with their WGM positions overlapping the narrow emission line of a laser source. The optical forces are created either evanescently or by focusing the laser beam close to the edge of microsphere where it can be efficiently coupled to WGMs.

Figure 3:
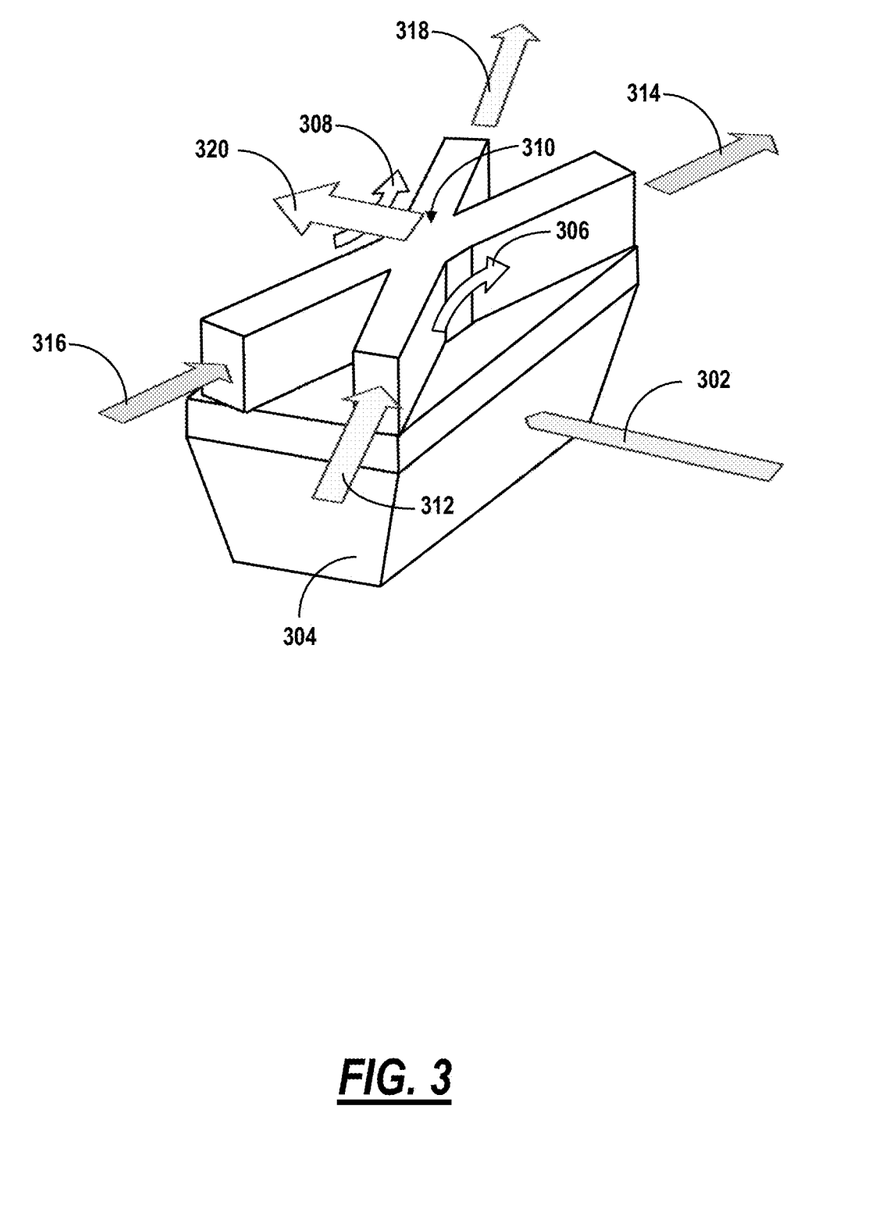
FIG. 3 is an illustration of the separating of microspheres by resonant optical forces in a microfluidic environment according to another embodiment.

FIG. 3 is an illustration of the separating of microspheres by resonant optical forces in a microfluidic environment according to another embodiment described herein. In FIG. 3, light 302 undergoes total internal reflection within an optical element 304, which is illustrated as a prism. An evanescent field is generated exterior to the optical element 304 in a vicinity of its surface. First and second fluidic flows 306 and 308 approach a point of contact 310 at which the two flows are tangential in the vicinity in which the evanescent field is generated. The first flow 306 has a fluidic incoming current 312 and a fluidic outgoing current 314. Similarly, the second flow 308 has a fluidic incoming current 316 and a fluidic outgoing current 318. Due to optical resonance, microspheres entrained in the incoming current 312 having WGM modes that strongly couple to the evanescent field are particularly affected by a force 320. As microspheres traverse the point of contact 310, the force 320 urges the resonant microspheres from the incoming current 312 of the first flow 306 to the outgoing current 318 of the second flow. When a heterogeneous mixture of microspheres is provided by the incoming current 312 of the first flow 306, resonant microspheres are separated from the mixture. The separated resonant particles are carried downstream from the point of contact 310 by the outgoing current 318 of the second flow.

Figure 4:
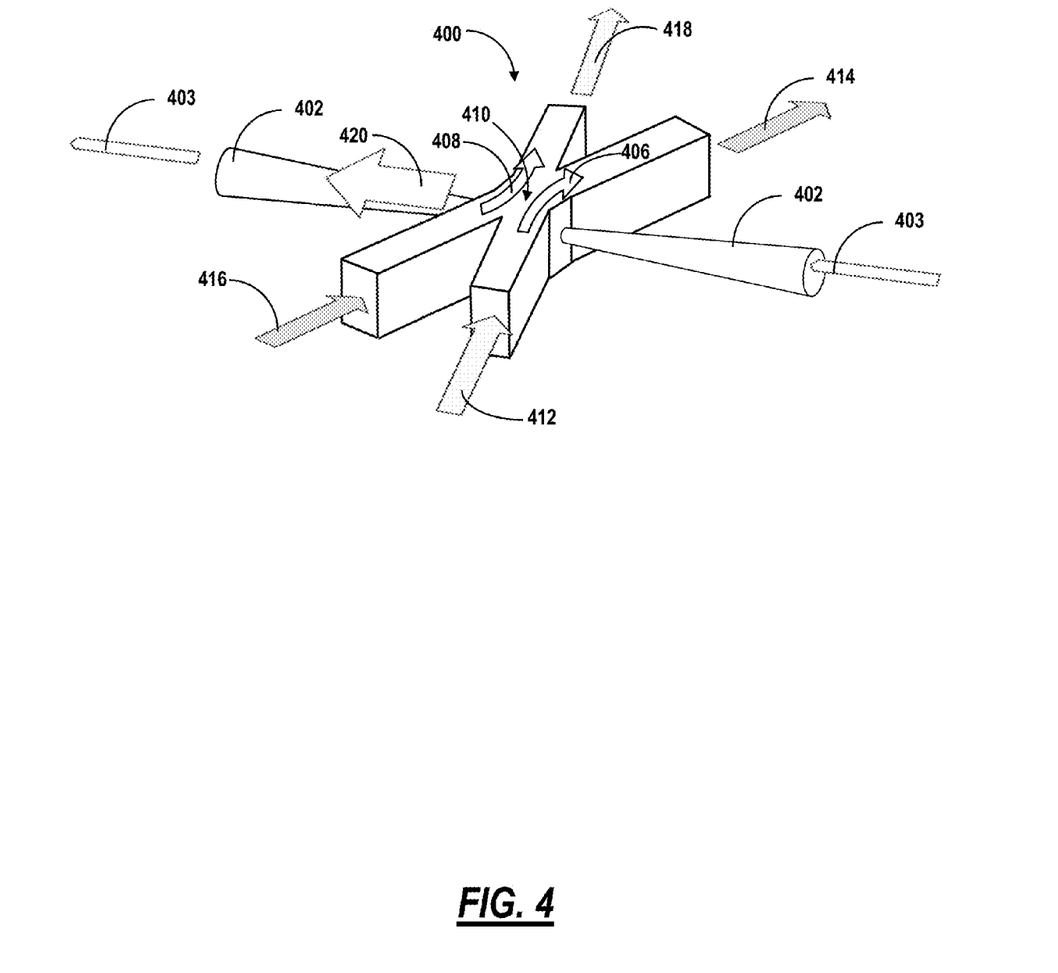
FIG. 4 is an illustration of the separating of microspheres by resonant optical forces in a microfluidic cell through which a tapered fiber passes according to yet another embodiment.

FIG. 4 is an illustration of the separating of microspheres by resonant optical forces in a microfluidic cell 400 through which a tapered fiber 402 passes according to yet another embodiment within the scope of these descriptions. The tapered fiber 402 passes through the sidewalls of the microfluidic cell 400. The structure is designed in such that guided light is not strongly leaking from the fiber at the points where the fiber is in contact with the material of sidewalls. This can be achieved by using relatively low index sidewall materials compared to the material of the tapered fiber or otherwise. When a laser beam 403 is guided by the tapered fiber 402, resonant light pressure is applied by an evanescent field to microspheres having WGM resonances that overlap with the emission line of the laser. In FIG. 4, first and second fluidic flows 406 and 408 approach a point of contact 410 at which the two flows are tangential. The first flow 406 has a fluidic incoming current 412 and a fluidic outgoing current 414. Similarly, the second flow 408 has a fluidic incoming current 416 and a fluidic outgoing current 418. Thus, the tapered fiber 402 traverses two liquid fluxes where they flow side-by-side. Microspheres are injected into the microfluidic cell 400 with the incoming current 412. Spheres with positions of WGM resonances overlapping with the emission line of the laser are dragged along the fiber by resonant light pressure at the point of contact 410 where the two currents make tangential contact. Such spheres are effectively separated from non-resonant spheres. As microspheres traverse the point of contact 410, the force 420 urges the resonant microspheres from the incoming current 412 of the first flow 406 to the outgoing current 418 of the second flow. When a heterogeneous mixture of microspheres is provided by the incoming current 412 of the first flow 406, resonant microspheres are separated from the mixture. The separated resonant particles are carried downstream from the point of contact 410 by the outgoing current 418 of the second flow 408. In another embodiment, a strip waveguide fabricated in the bottom plate of the microfluidic cell is used instead of a tapered fiber. Only microspheres moving close to the bottom of the cell are optically trapped and propelled along the strip waveguide. In another variation, the orientation of the tapered fiber or strip waveguide is not perpendicular, but along the microfluidic flux. In the latter case, the separation of the resonant microspheres would occur due to their motion against the direction of the flux in the fluidic channel. This separation can be even more efficient compared to perpendicular orientation because the resonant microspheres having high propelling velocity are able to move "against the stream," which means they could be delivered to a designated accumulation area by deliberate design. Various embodiments of microfluidic cells and many possible modifications, geometries and designs are within the scope of these descriptions. Specific embodiments and designs are provided expressly herein and in the drawings as examples of optofluidic sorters, but many geometries, and many optical and microfluidic delivery systems are within the scope of these descriptions.

Figure 5:
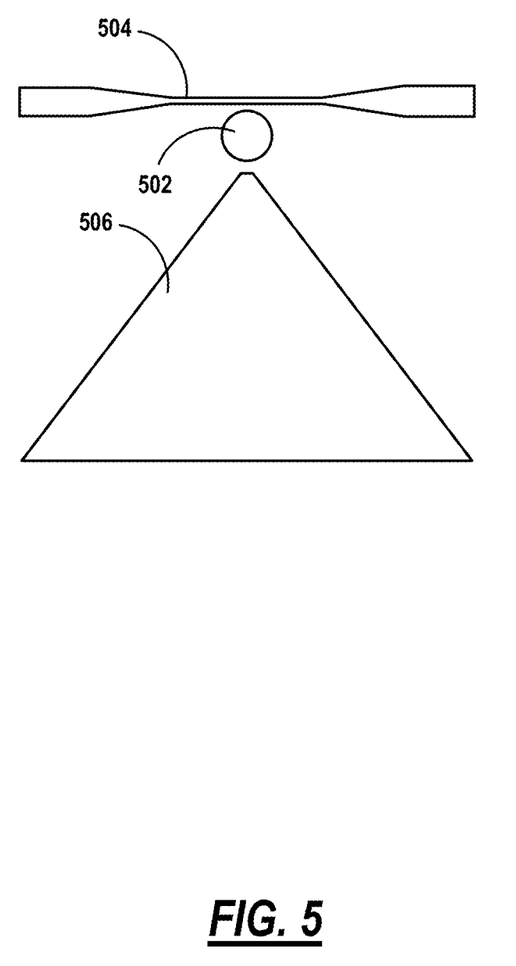
FIG. 5 is an illustration of the separating of microspheres by resonant optical forces using an optical tweezer according to another embodiment.

FIG. 5 is an illustration of the separating of microspheres by resonant optical forces using an optical tweezer according to another embodiment described herein. In this embodiment, microspheres 502 are brought into the evanescent field vicinity of a tapered fiber 504 or other evanescent waveguide structure using optical tweezers 506. By this technique, spectroscopic characterizations of the positions of WGM resonances are conducted for individual spheres using fiber-transmission spectroscopy. This technique also allows using a tunable laser source for sphere propulsion. In order to control the wavelength positions of WGM resonances in selected spheres, a laser source with a tunable spectral emission line can be used. Propulsion velocity is measured using a video system and the spheres with the WGM positions resonant with the laser are separated based on their higher propulsion velocity. The spheres propelled along the fiber are trapped, for example using another focused beam. In at least one example, the process is computerized and automated. Microspheres with any desired WGM positions are separated as determined by the wavelength of the tunable laser source.

Figure 6:
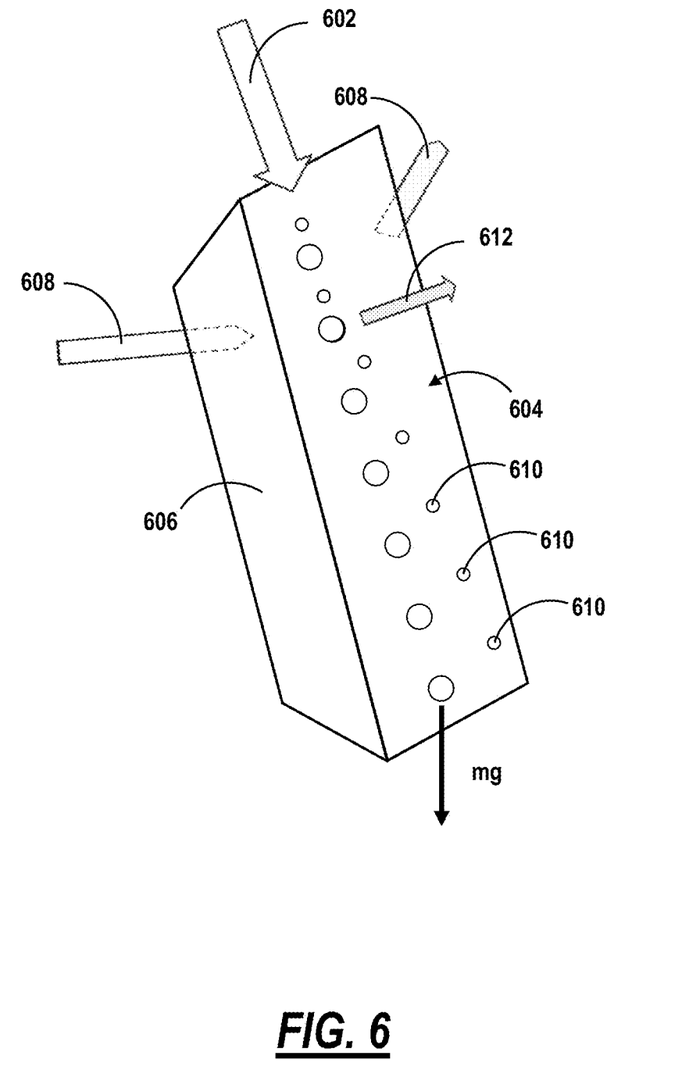
FIG. 6 is an illustration of the separating of microspheres at the surface of a prism along which a mixture of microspheres falls by gravity in air or in a vacuum according to another embodiment.

FIG. 6 is an illustration of the separating of microspheres by resonant optical forces applied at the surface of a prism along which a mixture of microspheres falls by gravity in air or in a vacuum according to another embodiment described herein. A heterogeneous mixture 602 of microspheres is provided at an inclined or vertical surface 604 of a prism 606 under gravity (mg). A beam of light 608 undergoes total internal reflection at the surface as illustrated in FIG. 6. In this design the spheres are moving in air (or vacuum) in a close vicinity to the surface 604. The resonant light pressure is exerted locally at the point of incidence of the focused laser beam with the surface 604. Consequently, the spheres 610 of a certain size acquire an x-component 612 of velocity that results in their efficient separation below the point of incidence. In another embodiment, instead of using total internal reflection, a laser beam is focused at the heterogeneous mixture of microspheres in a free falling motion. The maximal force on the microspheres would be exerted in the case of the laser beam waist passing close to the edge of microsphere where it can be efficiently coupled to WGMs. An optical element is not required in such an embodiment. Similarly, such spheres can be efficiently separated below the point of incidence.

Figure 7:
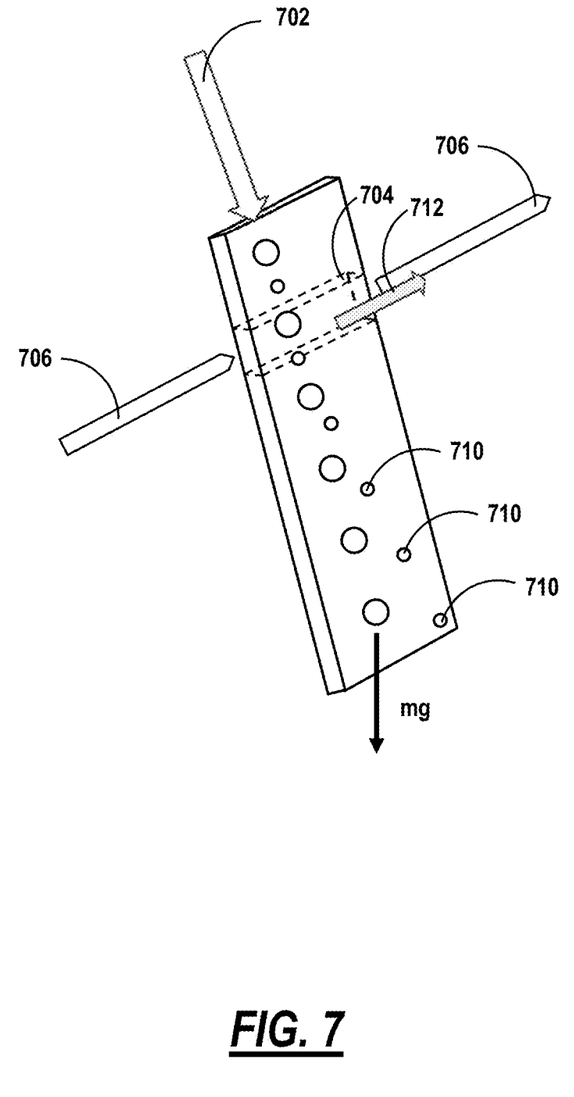
FIG. 7 is an illustration of the separating of microspheres at the surface of a waveguide structure along which a mixture of microspheres falls by gravity in air or in a vacuum according to yet another embodiment.

FIG. 7 is an illustration of the separating of microspheres by resonant optical forces applied at the surface of a waveguide structure along which a mixture of microspheres falls by gravity in air or in a vacuum according to yet another embodiment described herein. A heterogeneous mixture 702 of microspheres is provided under gravity (mg) in close vicinity to a surface stripe waveguide 704 that creates an evanescent field when a beam of light 706 propagates along the waveguide. The resonant light pressure along the waveguide results in efficient separation of spheres with desired positions of WGM resonances. Spheres 710 of a certain size acquire an x-component 712 of velocity that results in their efficient separation below their point of interaction with the evanescent field.

Figure 8:
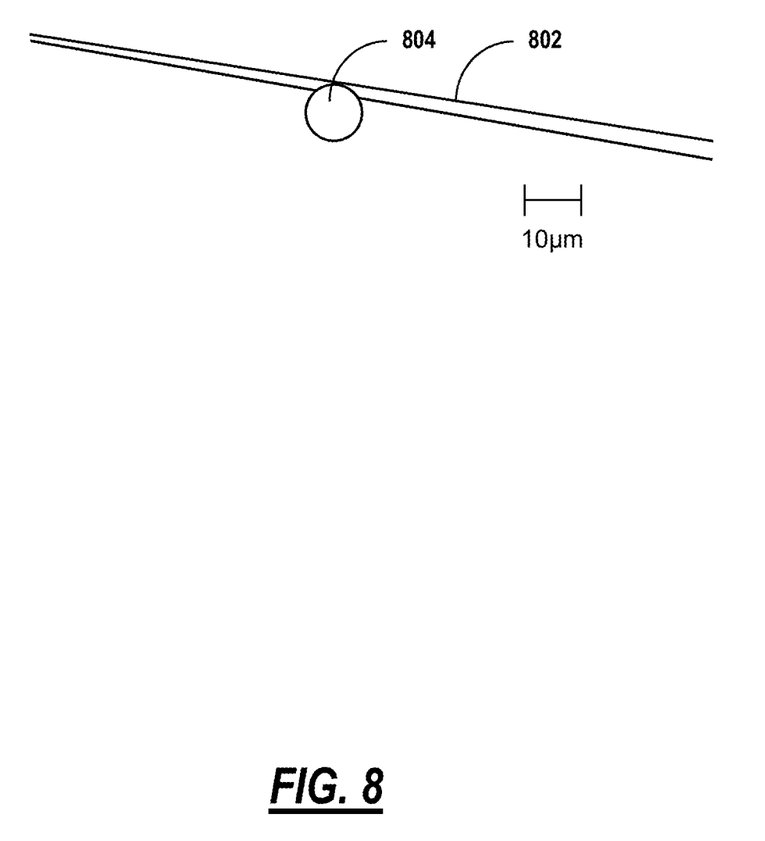
FIG. 8 is an illustration of a microsphere manipulate by resonant optical forces along a tapered optical microfiber.

FIG. 8 is an illustration of a microsphere manipulated by resonant optical forces along a tapered optical microfiber. The tapered fiber 802 was obtained by etching a single mode silica fiber in hydrofluoric acid. A 14.4 μm barium titanate glass microsphere 804 is attached to the tapered fiber inside a microfluidic environment. Micromanipulation was performed using another tapered fiber controlled by high-precision hydraulic micromanipulators. Narrow spectral resonances due to coupling to WGMs were detected in the fiber transmission spectra. A powerful tunable laser source is preferred for characterization of resonant light pressure effects.

Figure 9:
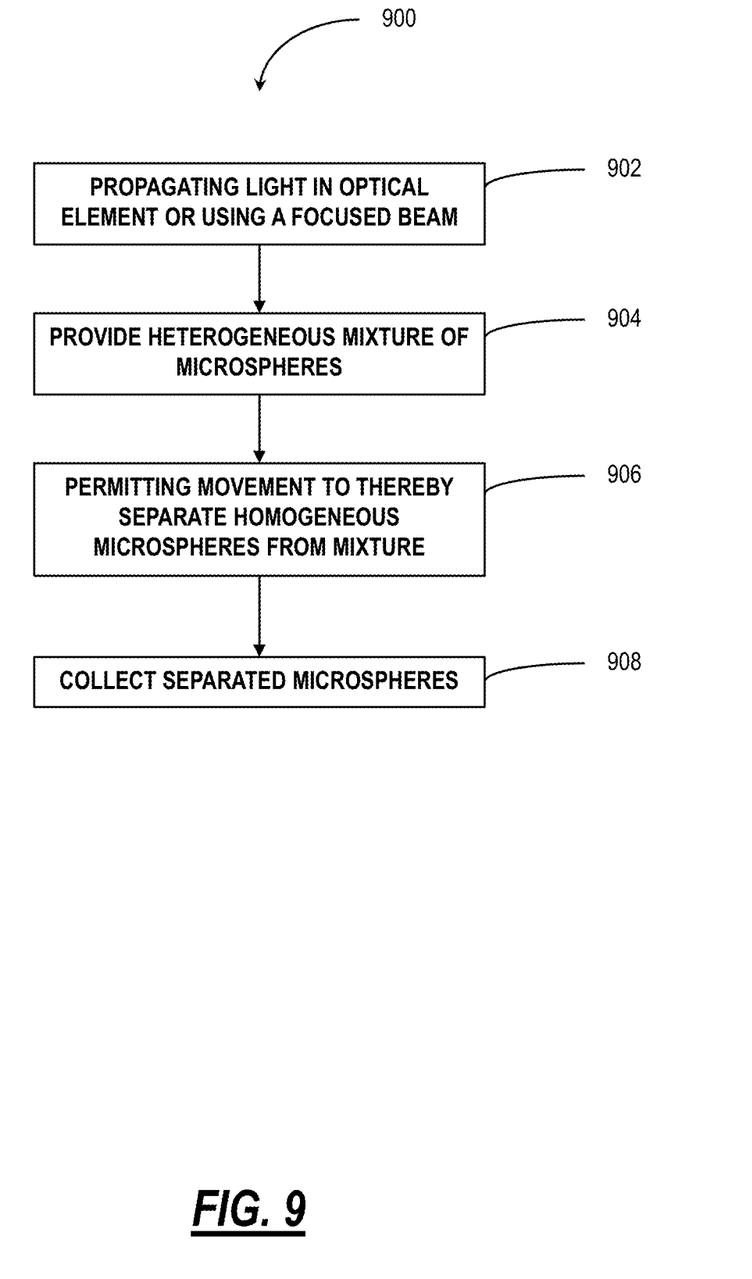
FIG. 9 is a flowchart illustrating a method of separating and collecting microspheres according to at least one embodiment.

FIG. 9 is a flowchart representing a method of separating and collecting microspheres according to at least one embodiment within the scope of these descriptions. The method 900 includes, in step 902, propagating light within an interior of an optical element at a surface of the optical element. An evanescent field exterior to the optical element is generated by the propagating light in a vicinity of the surface. Alternatively, an illumination of microspheres can be provided by an off-axially shifted focused laser beam to increase the resonant optical forces by efficient coupling to WGMs. In the latter case the optical element for creating evanescent fields is not required. The method 900 further includes, in step 904, providing a heterogeneous mixture of microspheres in the vicinity of the surface or in the vicinity of the focused laser beam. Each microsphere has a size and a refractive index. Forces are applied on at least some of the microspheres by the evanescent field according to size and refractive index. The method further includes, in step 906 permitting movement of at least some of the microspheres upon which forces are applied by the evanescent field, thereby separating at least some of the microspheres of the heterogeneous mixture from a remainder of the mixture according to at least one of size and refractive index. Either the separated microspheres, the remainder of the mixture, or both, are collected. In FIG. 9, step 908 represents collecting the separated microspheres.

Microspheres according to various embodiments described herein are useful in optoelectronic devices such as spectral filters, sensors, laser resonator arrays, and microspectrometers. Microspheres with almost resonant WGM peak positions can be assembled in controlled 1D, 2D, and 3D structures with engineered dispersions for photons. The principle of operation of such devices is based on resonant optical tunneling, or "hopping," of photons between microspheres even when separated by small distances. Advantageously, with regard to these structures as compared to conventional waveguides or to photonic crystal waveguides, the velocity of light can be controlled in coupled microspheres. Group velocity is determined by the coupling constant between WGMs in microspheres. So, by controlling the separation between microspheres or by controlling the properties of the surrounding medium, one can control the velocity of light in assembled structures. Other properties of structures formed by multiple spheres include very steep spectral filtering properties. These structures are analogous to high-order filters in circuit engineering and provide very strong and spectrally abrupt rejection of light outside narrow transmission windows. Strong spectral filtering properties are desired in many applications for reducing signal-to-noise ratios and for filtering different spectral signatures.

Multiple spheres can be also used as sensitive sensors of nanoparticles, cells, and proteins. Once these particles are deposited on the sidewall surfaces of coupled microspheres, tiny changes in the spectral properties of WGMs occur. Such changes can be sensitively detected due to the extremely high Q-factors. Such particles can cause spectral shifts and broadening effects for WGM resonances detected using, for example, a tapered fiber. In some cases, however, nanoparticle binding events can cause splitting effects in the WGM spectra. All these spectral effects can be used to determine the size and refractive index of the nanoparticles. Multiple spheres with preselected WGM peak positions can increase the functionality and usefulness of such sensors.

Microspheres with matched positions of WGM resonances can be used in laser resonator arrays. Large-scale 2D arrays and 3D crystal-like structures formed by such spheres can be very efficient light-emitting devices due the fact that WGM resonances are coupled on a massive scale in such structures. Microspheres can be used to control light extraction efficiency, directionality, yield, photon life time, and properties of coupling of photonic modes to the light-emitting species (quantum dots or dye molecules) embedded in such structures. Microspheres can be deposited or self-assembled at the top of a semiconductor light-emitting structure to change or control its characteristics. Furthermore, microspheres with preselected positions of WGM resonances can be used for building a compact microspectrometer, in which each sphere resonates at a series of WGM resonant wavelengths, so the spatial pattern of WGMs excited in different spheres can provide information about a spectrum of unknown source. Due to high Q-factors of WGMs, very high spectral resolution can be achieved. It should be noted that the mainstream effort in this direction is based on using "hard" semiconductor fabrication techniques such as photolithography, electron beam lithography, reactive ion etching, etc. These methods allow fabrication of microrings, disks or toroids integrated on the same chip. However the reproducibility of the cavity dimensions over millimeter-scale wafers is limited in all these techniques at approximately 0.1% level of uniformity. This remains true even for the best established methods such as in-plane silicon CMOS-compatible fabrication. Thus, the methods and devices according to embodiments described herein represent a new alternative technology for developing coupled-cavity structures which has many advantages over conventional technologies: 10 times better uniformity of the cavities; possibility to integrate spheres in all three spatial dimensions; and reduced cost of fabrication. Many uses and advantages in research and commerce will be appreciated by optoelectronics research teams at universities and commercial laboratories.

Microspheres are useful in biomedical applications. Microspheres with preselected positions of WGM resonant peaks are required in a wide range of biomedical endeavors where they are used as markers, fluorescent labels, and spectral fingerprints. They are also used in spectral sensors of bacteria, proteins and cells. Many uses and advantages in research and commerce will be appreciated by the research teams at biomedical companies and universities.

Microspheres are useful in metrology and size standardization. Particle size standards may be used to validate sizing instruments across their dynamic ranges. Spectral positions of WGM peaks are determined by the diameters of the spherical cavities. Practical microsphere resonators are generally considered perfect spheres despite their possible ellipticity. So, selection of the spheres by the position of their WGM resonance also means sorting by size. However, the resonant WGM peak positions in different spheres can be characterized with different angular numbers. Nonetheless, very nearly identical spheres can be selected by this technique. Such spheres are suitable for use in the performance of routine instrument calibration checks and corrections, and in the support of practice standards, such as those published by the International Organization for Standardization (ISO), the American Society for Testing and Materials (ASTM) International, the European Committee for Standardization (CEN), and other organizations. Additionally, the use of reference material permits the standardization of results between runs, instruments, laboratories, and over time.

Although the present disclosure has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present disclosure, are contemplated thereby, and are intended to be covered by the following claims.

The invention claimed is:

1. A method of separating and collecting microspheres comprising:
propagating light within an interior of an optical element at a surface of the optical element, thereby generating an evanescent field exterior to the optical element in a vicinity of the surface;
providing a heterogeneous mixture of microspheres in the vicinity of the surface within the evanescent field, each microsphere having a size and a refractive index, thereby applying forces on at least some of the microspheres by the evanescent field according to size and refractive index;
permitting movement of at least some of the microspheres upon which forces are applied by the evanescent field, thereby separating at least some of the microspheres of the heterogeneous mixture from a remainder of the mixture according to at least one of size and refractive index; and
collecting at least one of: the separated microspheres; and the remainder of the mixture;
wherein providing a heterogeneous mixture of microspheres comprises providing free falling microspheres.

2. A method according to claim 1, further comprising selecting a frequency of the propagating light to match an optical resonance of particular ones of the microspheres.

3. A method according to claim 2, further comprising selecting a frequency of the propagating light to match a whispering gallery mode (WGM) optical resonance of particular ones of the microspheres.

4. A method according to claim 3, wherein the particular ones of the microspheres are forced by the evanescent field from a first fluid flow in which the heterogeneous mixture is provided to a second fluid flow in which the particular ones are collected as the separated microspheres.

5. A method according to claim 1, wherein propagating light within an interior of an optical element at a surface of the optical element comprises propagating light by internal reflection.

6. A method according to claim 1, wherein propagating light within an interior of an optical element comprises propagating light within a waveguide, prism, or tapered fiber.

7. A method according to claim 1, wherein:
propagating light within an interior of an optical element comprises propagating light along a strip waveguide or tapered fiber, and
providing a heterogeneous mixture of microspheres comprises providing a flow of microspheres in a direction opposite to the direction of the propagating light such that permitting movement of at least some of the microspheres comprises movement of at least some of the microspheres against the provided flow.

8. A method according to claim 1, further comprising:
flowing, in the vicinity of the surface, a first fluid in which the heterogeneous mixture is provided; and
flowing, in fluid contact with the first fluid, a second fluid in which the separated microspheres are collected.

9. A method according to claim 8, wherein:
the second fluid flows tangentially to the first fluid at a point of fluid contact between the first and second fluid; and
at the point of fluid contact, forces perpendicular to the first fluid are applied on at least some of the microspheres by the evanescent field.

10. A system for separating and collecting microspheres comprising:
an optical element having an interior bounded by a surface;
a light source coupled to the optical element, the light source propagating light of a particular frequency within the interior at the surface thereby generating an evanescent field exterior to the optical element in a vicinity of the surface; and
a heterogeneous mixture of microspheres flowing exterior to the optical element in the evanescent field in the vicinity of the surface, each microsphere having a size and a refractive index;
wherein the particular frequency is selected to match a resonant frequency of at least some of the microspheres according to size and refractive index to apply forces by the evanescent field to the microspheres for which the resonant frequency is matched;
wherein the heterogeneous mixture of microspheres comprises free falling microspheres.

11. A system according to claim 10, wherein the optical element comprises a waveguide, prism, or tapered fiber.

12. A system according to claim 10, wherein the optical element comprises a strip waveguide or tapered fiber along which light propagates perpendicular or parallel to a direction in which the heterogeneous mixture of microspheres flows.

13. A system according to claim 10, wherein the heterogeneous mixture of microspheres comprises microspheres of different sizes.

14. A system according to claim 10, wherein the light source is frequency-matched to a whispering gallery mode (WGM) optical resonance of microspheres having a particular size.

15. A system according to claim 10, wherein the heterogeneous mixture of microspheres free falls in a gaseous or vacuum environment.

16. A system according to claim 10, wherein the microspheres comprise at least one of barium-titanate glass and titania.

17. A system according to claim 10, further comprising an optical tweezer that catches microspheres propelled by the evanescent field and delivers the caught microspheres to another location.

* * * * *